(12) United States Patent
Yuan et al.

(10) Patent No.: US 11,849,983 B2
(45) Date of Patent: Dec. 26, 2023

(54) BONE FIXATION SYSTEM AND METHOD

(71) Applicant: Field Orthopaedics Pty Ltd, Teneriffe (AU)

(72) Inventors: Huan Yuan, Keperra (AU); Owen John Bawden, New Farm (AU); Kelly Coverdale, Holland Park (AU); Christopher Arnold Jeffery, Newstead (AU); Jarred James Bairstow, Holland Park (AU); Jayaraman Somu, Chennai (IN); Shanthan Pather, Morningside (AU)

(73) Assignee: Field Orthopaedics Pty Ltd, Teneriffe (AU)

( * ) Notice: Subject to any disclaimer, the term of this patent is extended or adjusted under 35 U.S.C. 154(b) by 11 days.

(21) Appl. No.: 17/404,522

(22) Filed: Aug. 17, 2021

(65) Prior Publication Data
US 2022/0054176 A1 Feb. 24, 2022

(30) Foreign Application Priority Data
Aug. 18, 2020 (AU) ................................ 2020902937

(51) Int. Cl.
*A61B 17/80* (2006.01)
*A61B 17/88* (2006.01)

(52) U.S. Cl.
CPC .......... *A61B 17/8052* (2013.01); *A61B 17/88* (2013.01)

(58) Field of Classification Search
CPC ...... A61B 17/80; A61B 17/8052; A61B 17/88
See application file for complete search history.

(56) References Cited

U.S. PATENT DOCUMENTS

| | | | |
|---|---|---|---|
| 8,425,576 B2* | 4/2013 | Anderson | A61B 17/8052 606/294 |
| 9,924,984 B2* | 3/2018 | Hartdegen | A61B 17/8625 |
| 10,743,922 B1* | 8/2020 | Touchet | A61B 17/8052 |
| 11,331,127 B2* | 5/2022 | Wang | A61B 17/8605 |
| 2016/0081722 A1* | 3/2016 | Josse | A61B 17/7059 606/246 |
| 2016/0317205 A1* | 11/2016 | Baker | A61B 17/8061 |
| 2017/0238979 A1* | 8/2017 | Laird | A61B 17/8052 |
| 2021/0121205 A1* | 4/2021 | Ramare | A61F 2/4455 |
| 2022/0233222 A1* | 7/2022 | Papannagari | A61B 17/8052 |

* cited by examiner

*Primary Examiner* — Larry E Waggle, Jr.
(74) *Attorney, Agent, or Firm* — Best & Flanagan LLP

(57) ABSTRACT

A bone fixation system for bone repair, the system comprising a bone fixation plate with upper and lower surfaces and at least one opening formed on the upper and lower surfaces to form a passage extending from the upper surface to the lower surface to receive a bone screw. The passage is defined by one or more non-threaded inner walls extending from the upper surface to the lower surface. At interference portions, the passage has a width between the walls smaller than the diameter of the head of the bone screw to achieve interference between the head of the bone screw and the inner walls at interference portions to lock the bone screw within the passage upon its insertion into the passage at a variable angle of rotation relative to a longitudinal axis of the passage.

14 Claims, 10 Drawing Sheets

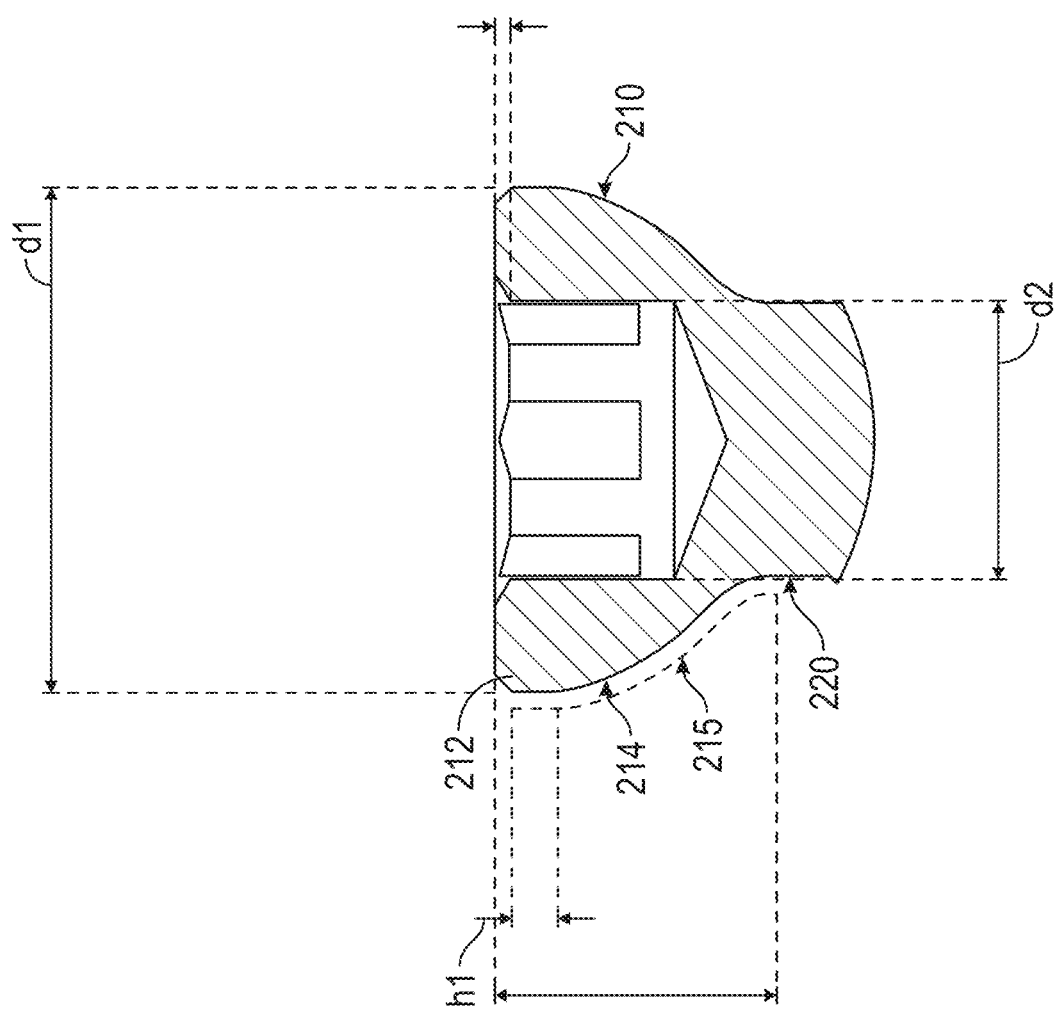

BONE FIXATION SYSTEM AND METHOD

CROSS-REFERENCE

This application claims the benefit of Australian provisional Patent Application Serial No. 2020902937, filed Aug. 18, 2020, for "BONE FIXATION SYSTEM AND METHOD" by Huan Yuan, Owen John Bawden, Kelly Coverdale, Christopher Arnold Jeffery, Jarred James Bairstow, Jayaraman Somu, and Shanthan Pather, the disclosure of which is incorporated herein by reference.

TECHNICAL FIELD

The present invention relates to a locked bone fixation assembly, and in particular to an assembly that allows for a surgeon-selected angle of the bone screw relative to the fixation device.

BACKGROUND

Any references to methods, apparatus or documents of the prior art are not to be taken as constituting any evidence or admission that they formed, or form part of the common general knowledge.

Bone fixation systems for the internal fixation of bone fractures are known. Such systems are particularly well-suited to promote the healing of a fracture. A bone screw (also known as a bone anchor) is inserted through a bone plate hole (also known as an anchor hole or a screw hole) and is threaded into bone to compress, neutralize, buttress, tension bend, and/or bridge the fracture ends together and draw the plate against the bone. These screws are not secured or locked to the bone plate and can be threaded into bone at various angles relative to the bone plate. However, because the screws are not secured to the bone plate, the angular relationships between the plate and screws are not fixed and can change intraoperatively and/or postoperatively. That is, dynamic loading on the bone and bone plate from physiological conditions can cause the screws to loosen or back out with respect to the plate ultimately leading to poor alignment and poor clinical results.

Securing the screws to the plate provides a fixed angular relationship between the screws and plate and reduces the incidence of loosening. One known method of securing the screw with the bone plate is the use of screw threads on the screw head which can be secured with threads provided along inner walls defining the screw holes of the bone plate. These screws commonly referred to as "locking screws" are typically inserted coaxially with the central axis of the hole. Because the relationship between locking screws and the plate is fixed, the locking screws and plate act as a single unit which provides high resistance to shear, torsional, and bending forces. However, such locking screws are limited in their ability to compress bone fragments, which affects healing. Moreover, bone plates that use locking screws such as the system described in U.S. Pat. No. 9,155,577 which allow variable angle fixation are normally very thick. Here are the advantages of the reconstruction plates: Bone fixation plates are relatively massive plates, typically made of a hard titanium grade or titanium alloys with a material thickness of 2.0 to 3.5 mm, which are very stable and can absorb high forces. These reconstruction plates are usually designed so that the bending areas lie between the screw holes, wherein the openings and bending areas strung together like a string of pearls. The bending zones allow the plate to be anatomically adapted to the bone fragments, opening to opening.

Despite their specially designed deformation areas, reconstructive plates are difficult to adapt to the particular bone shape. To bend the plates very high forces may be required due to the material thickness and the material strength. Due to the large forces required, the bending tools must be designed to be strong, accurately fitting and with corresponding lever paths. Thicker bone plates are also known for causing irritation to surrounding soft tissues which leads to high rates of bone plate removal. As a result, it is desirable to provide bone fixing plates with a lower profile that can allow variable angle locking of the screw head.

Another issue associated with currently available bone plates that allow variable angle locking of the screw head relates to reusability of the bone plate. Often, the orthopaedic surgeon may need to change the orientation of the screw after an initial drilling operation. Many of the currently available bone plates that allow variable angle locking do not allow the same screw holes to be used repeatedly because the threads or the other engagement mechanisms become permanently damaged after a single use.

Yet another issue with some of the currently known bone plates and associated bone screws is that their screw head locking mechanisms function independently of the compression mechanism of the bone screw. As a result, the screw head in some instances may lock with the hole of the bone plate even though the screw has not fully compressed the bone plate.

In view of the above, it is desirable to provide an improved bone fixation system that addresses at least some of the problems of the prior art.

SUMMARY OF INVENTION

In an aspect, the invention provides bone fixation system for reconstruction and/or trauma treatment of bones, the system comprising: a bone fixation plate configured and dimensioned for application to a patient's bone, the bone plate comprising an in-use upper surface and an in-use lower surface with at least one opening formed on the upper and lower surfaces to form a passage extending from the upper surface to the lower surface; each passage being defined by one or more non-threaded inner walls extending from the upper surface to the lower surface of the bone plate to receive a bone screw; and resiliently deformable interference portions located along an in-use upper portion of the one or more inner walls, the interference portions being dimensioned to define the width of the passage to be smaller than the diameter of the head of the bone screw to achieve deformation of the interference portions and interference between the head of the bone screw and the inner walls to lock the head of the bone screw within the passage upon insertion of the bone screw into the passage at a variable angle of rotation relative to a longitudinal axis of the passage that is substantially perpendicular to the upper surface of the bone plate.

In an embodiment, each opening is defined by a plurality of inner walls such that adjacently located inner walls are separated by a recessed channel.

In an embodiment, the recess extends between the upper surface and the lower surface of the bone plate.

In an embodiment, the recess is substantially parallel to an imaginary longitudinal axis passing through the opening.

In an embodiment, the bone fixation system comprises a plurality of said recesses, the recesses being circumferentially arranged relative to the opening of the bone plate.

In an embodiment, portions of the one or more inner walls comprise a curved surface.

In an embodiment, the one or more inner walls comprises a concave surface.

In an embodiment, the upper portions of the inner walls comprise a concave spherical surface.

In an embodiment, said portions of the innerwalls of the opening converge towards in an in-use downwardly direction from the upper surface to the lower surface thereby decreasing the diameter of the opener in an in-use downwardly direction.

In an embodiment, diameter of the opening defined by the inner walls gradually deceases in an in-use downwardly direction from the upper surface to the lower surface.

In an embodiment, the inner walls define a convergent passage converging towards the lower surface of the bone plate for engaging the head of the bone screw.

In an embodiment, said portions of the inner walls defining the opening on the upper wall into the passage to be smaller than the diameter of the head of the bone screw comprise a substantially planar surface positioned for abutment with an upper rim of the head of the bone screw.

In an embodiment each said interference portion is located in an in-use upper portion of the corresponding inner wall.

In an embodiment, said interference portions of the inner wall are formed from deformable material such that interference between the head of the bone screw during use results in deformation of at least the said portions to allow the head of the bone screw to be locked into the passage.

In an embodiment, the bone fixation system comprises a plurality of the interference portions being circumferentially arranged relative to the opening of the upper surface, the interference portions being along the inner walls defining the passage such that upon insertion of the bone screw at a variable angle of rotation relative to a longitudinal axis of the passage that is substantially perpendicular to the upper surface of the bone plate and the head of the bone screw engages one or more of said portions thereby locking the head of the bone screw with the inner walls.

In an embodiment, the opening of the upper edge of the head of the bone screw comprises a bevelled or filleted edge.

In an embodiment, the head of the bone screw comprises a planar in-use upper portion an a curved in-use lower portion such that upon insertion of the bone screw into the opening, the planar upper portion of the head of the screw engages with said portions of the inner wall to lock the head with the inner walls defining the passage.

In an embodiment, the curved lower portion of the head is a substantially spherical surface configured to allow the lower portion of the head to be seated into the passage along the inner walls.

In another aspect, there is provided a method of affixing a bone screw to a bone fixation plate at a desired orientation, comprising the steps of: providing a bone screw comprising a non-threaded head portion with a driver engaging interface and an adjoining elongate threaded shank section comprising helical threads; providing a bone fixation plate comprising an in-use upper surface and an in-use lower surface with at least one opening formed on the upper and lower surfaces to form a passage extending from the upper surface to the lower surface; each passage being defined by one or more non-threaded inner walls extending from the upper surface to the lower surface of the bone plate to receive the bone screw; and resiliently deformable interference portions located at in-use upper portions of the one or more inner walls are dimensioned to define the width of the passage to be smaller than the diameter of the head of the bone screw; positioning said bone fixation plate on bone tissue such that the in-use lower surface of the bone fixation plate is positioned to contact and engage the bone tissue and positioning the in-use upper surface for receiving the shank portion of the bone screw; selecting one of a plurality of different insertion angles at which the bone screw is to be inserted into the passage of the bone fixation plate; inserting the elongate shank of the bone screw into the a passage opening located on the upper surface of the bone fixation plate at the selected insertion angle and applying drive to the head of the bone screw until interference is achieved between an outer surface of the head of the bone screw and the interference portions of the inner walls of the bone fixation plate to deform the interference portions and lock the head of the bone screw within the passage upon insertion of the bone screw into the passage at the selected angle of insertion.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 8A is an enlarged view of the head 210 of the bone screw 200.

DETAILED DESCRIPTION OF PREFERRED EMBODIMENTS

Figure 1:
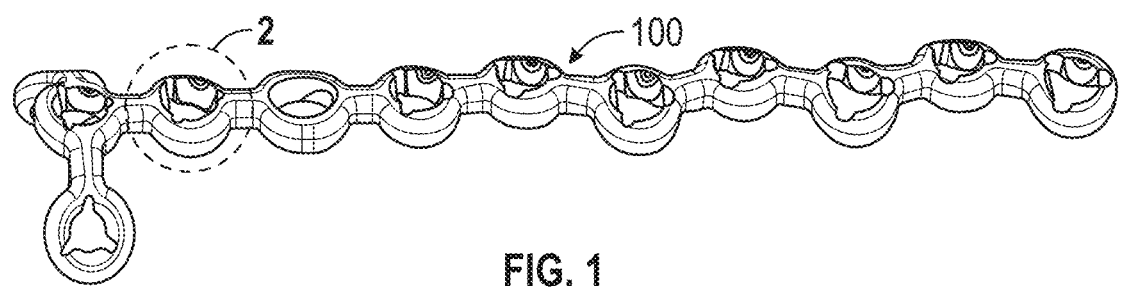
FIG. 1 is a top perspective view of a bone fixing plate 100 that forms a part of the bone fixation system 100 in accordance with the first embodiment.
Figure 2:
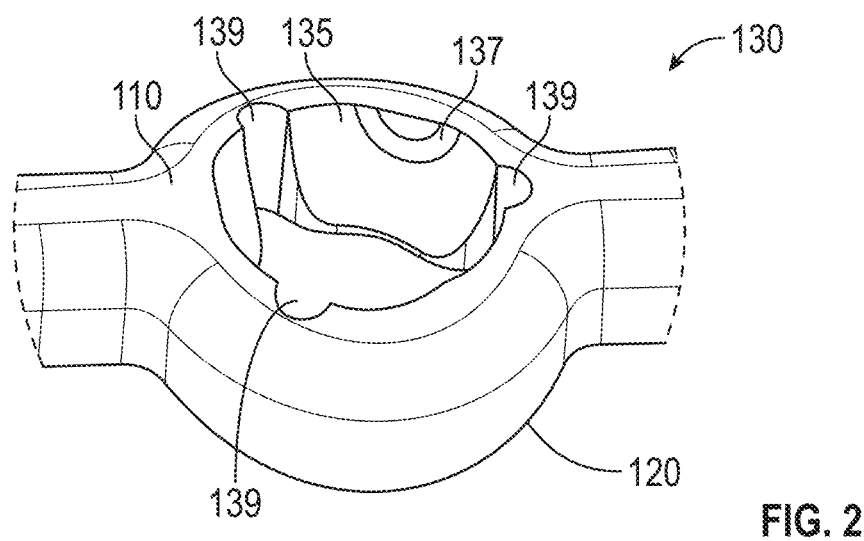
FIG. 2 is an enlarged view of inset E shown in FIG. 1.
Figure 3:
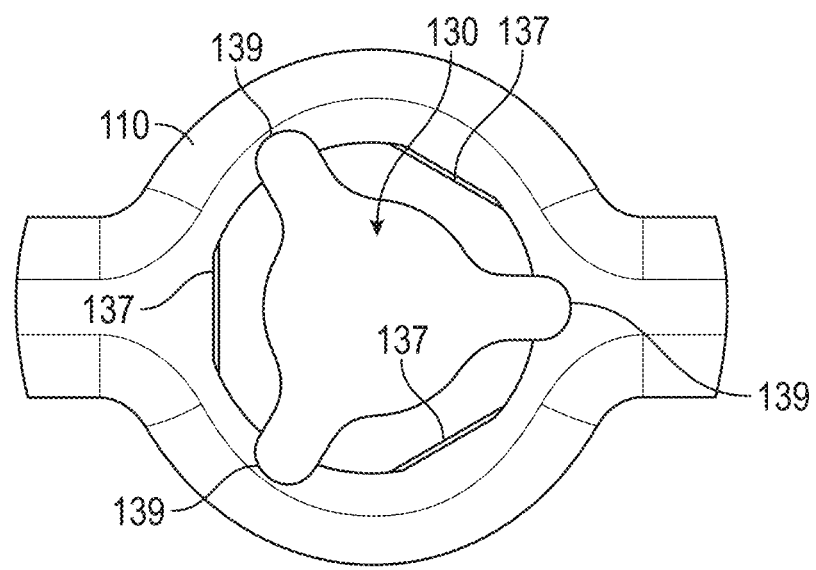
FIG. 3 is a top view (enlarged) of a plate hole 130 for the bone fixing plate 100.
Figure 4:
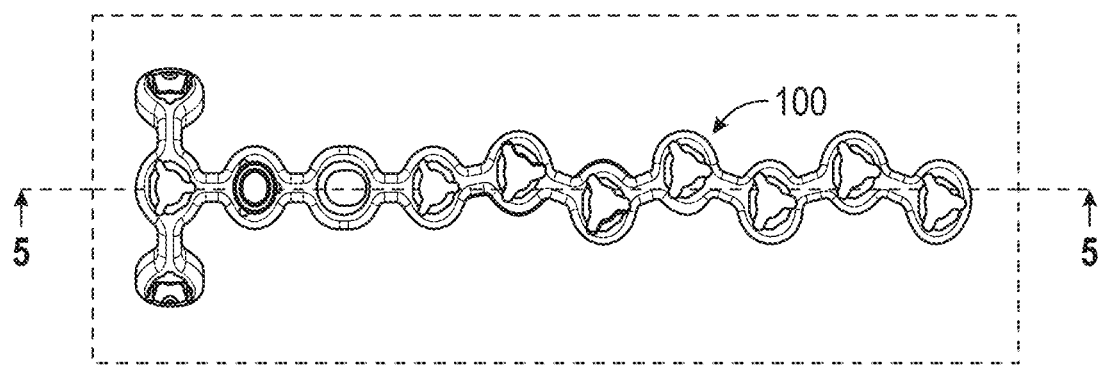
FIG. 4 is a top view of the bone fixing plate 100.
Figure 5:
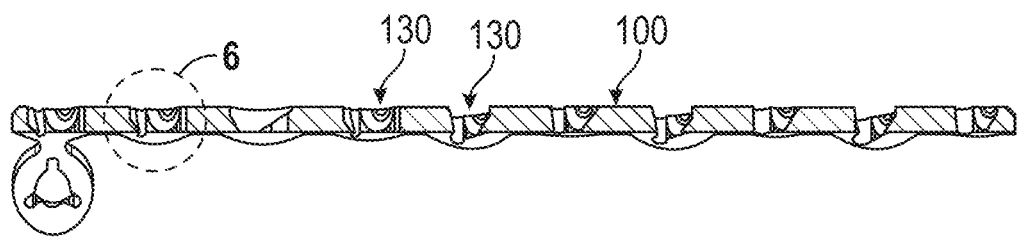
FIG. 5 is a sectional view of the bone fixing plate 100.
Figure 6:
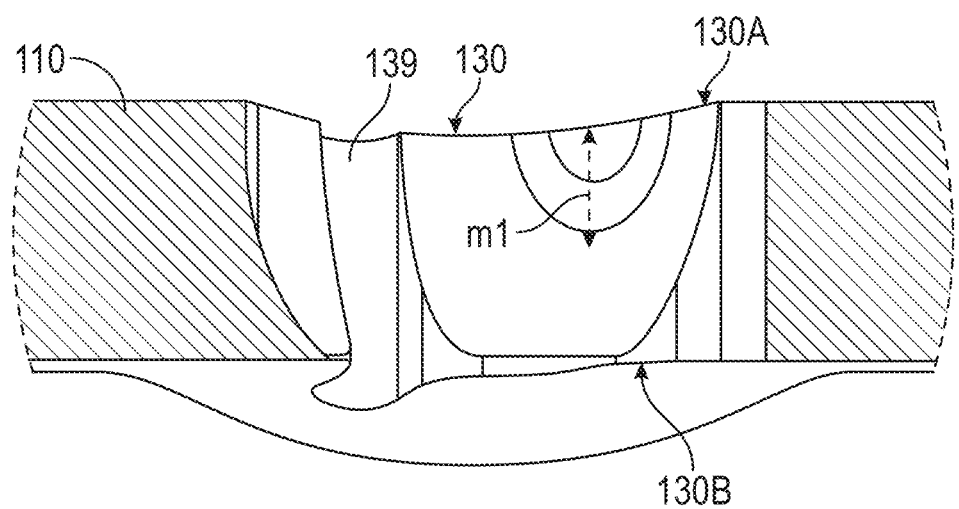
FIG. 6 is an enlarged sectional view of the plate hole 130 from inset D shown in FIG. 5.
Figure 7:
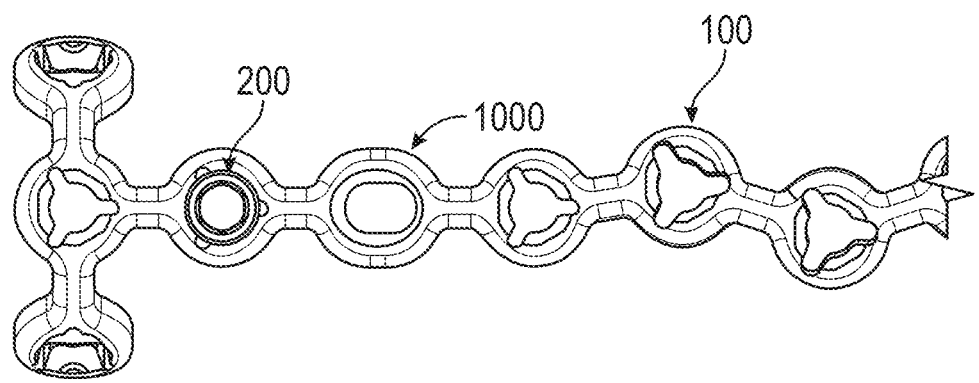
FIG. 7 is a top view of the bone fixation system 100 including the bone fixing plate 100 and the locking bone screw 200.
Figure 8:
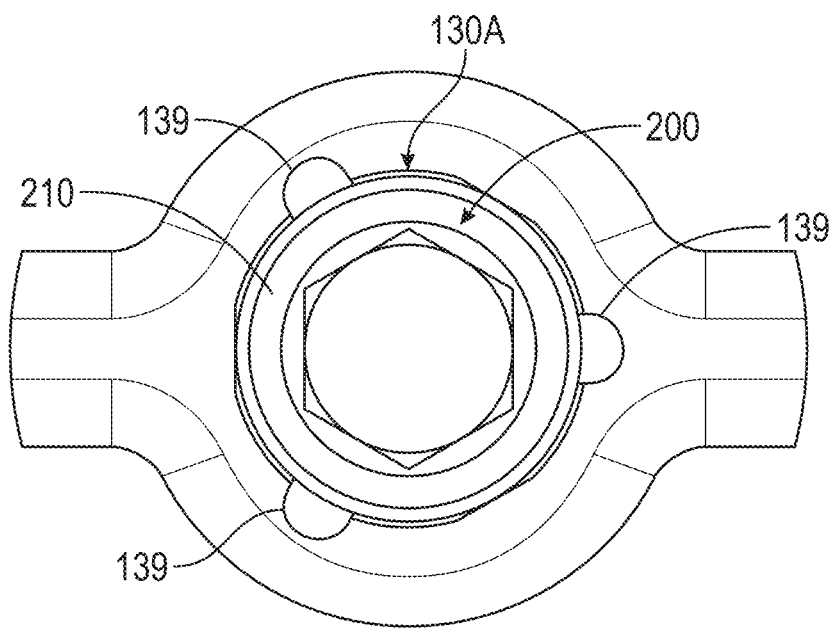
FIG. 8 an enlarged top view of the bone screw 200 in a locked position within the screw hole 130 of the bone fixing plate 100.
Figure 9:
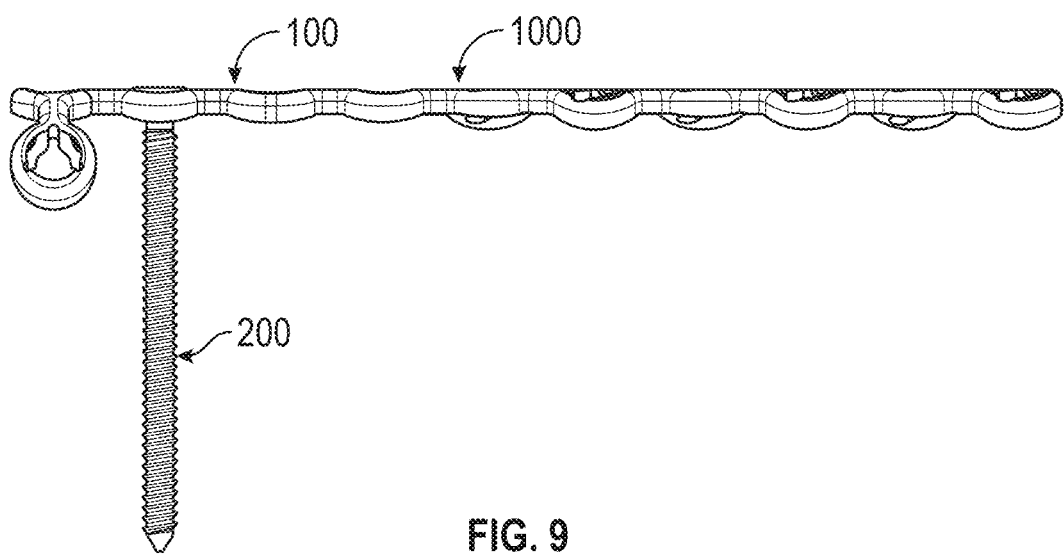
FIG. 9 is a side view of the bone fixation system 1000.
Figure 10:
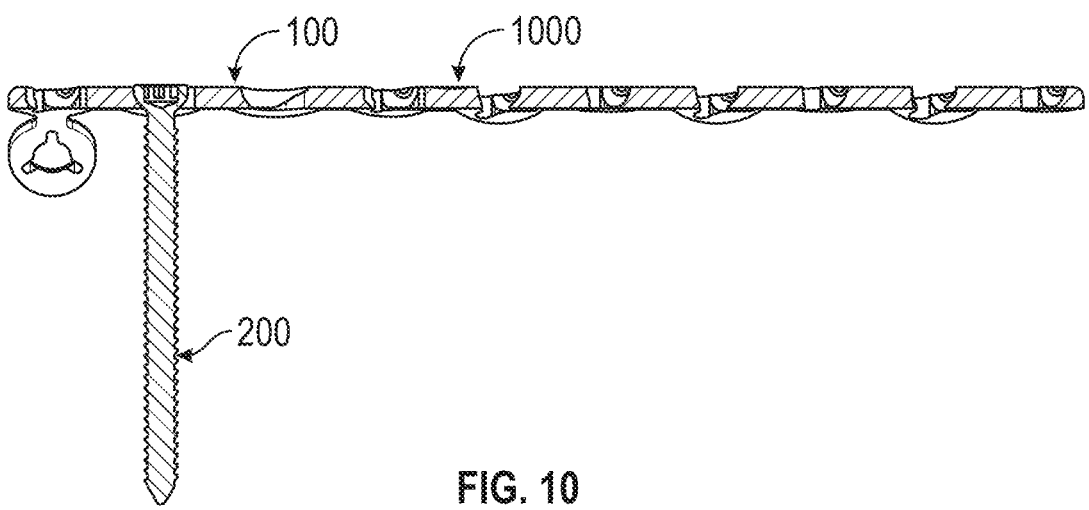
FIG. 10 is a sectional view of the bone fixation system 1000 shown in FIG. 9 in which the bone screw 200 is locked with the screw hole 130 in a substantially perpendicular position.
Figure 11:
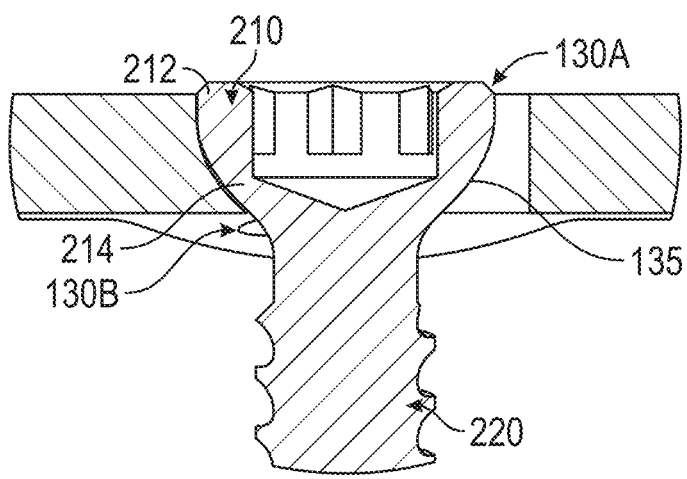
FIG. 11 is an enlarged sectional view of the bone fixation system 1000.
Figure 12:
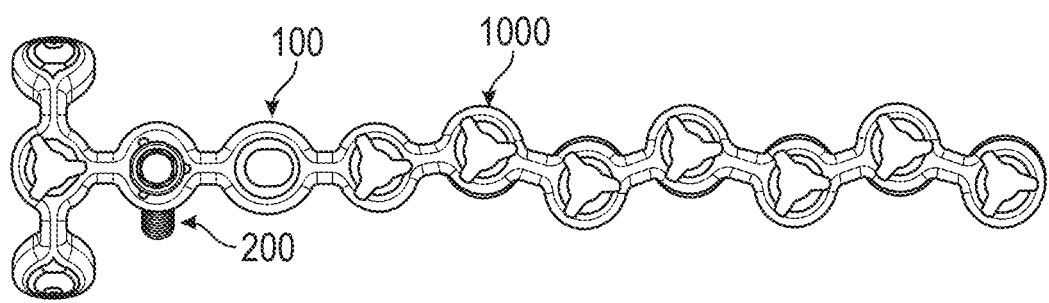
FIG. 12 is a top view of the bone fixation system 1000 in which the bone screw 200 is locked at an acute angle relative to the longitudinal axis of the screw hole 130.
Figure 13:
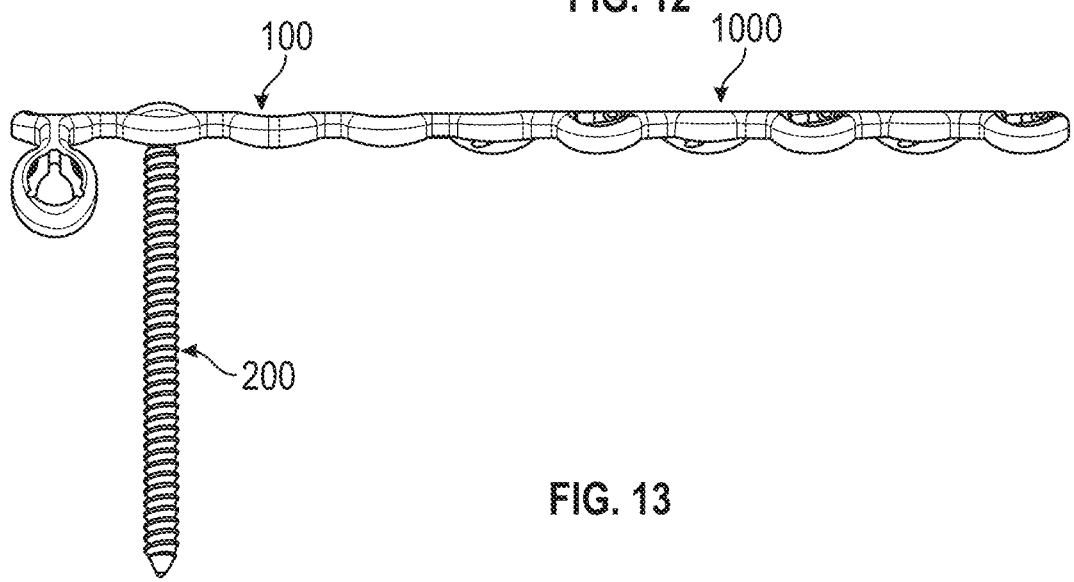
FIG. 13 is a side view of the bone fixation system 1000 shown in FIG. 12.
Figure 14:
FIG. 14 is a sectional view of the bone fixation system shown in FIG. 13.
Figure 15:
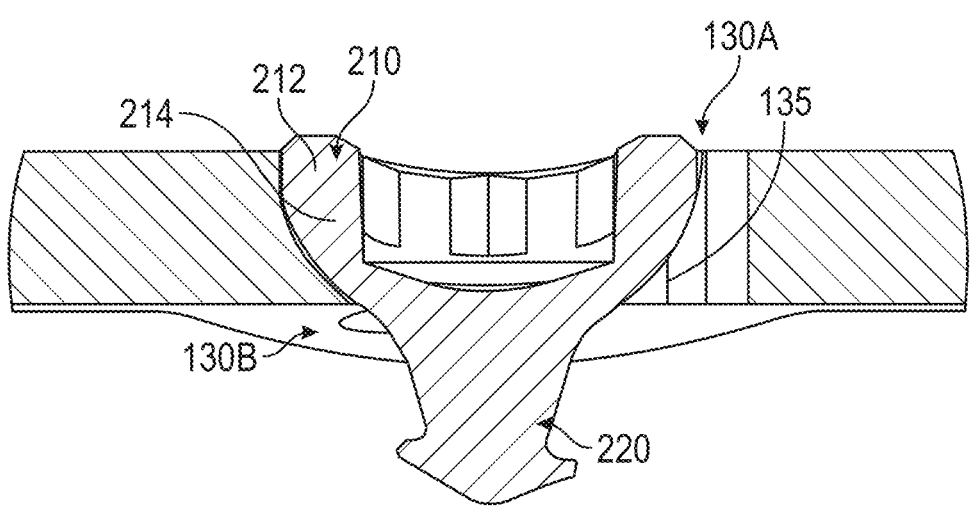
FIG. 15 is an enlarged sectional view of the bone fixation system shown in FIG. 14.
Figure 16:
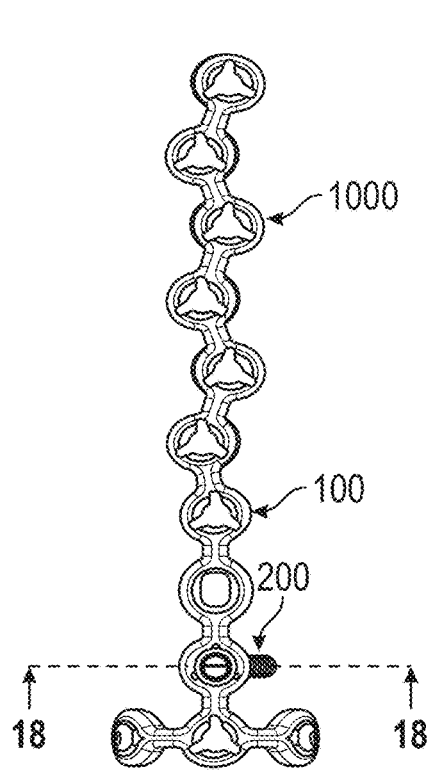
FIG. 16 is a top view of the bone fixation system 100 in which the bone screw 200 is locked at an acute angle relative to the longitudinal axis of the screw hole 130.
Figure 17:
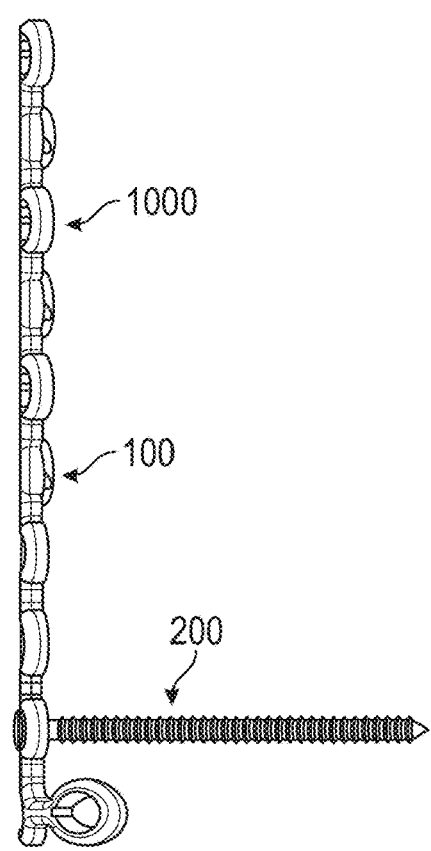
FIG. 17 is a side view of the bone fixation system 1000 shown in FIG. 16.
Figure 18:
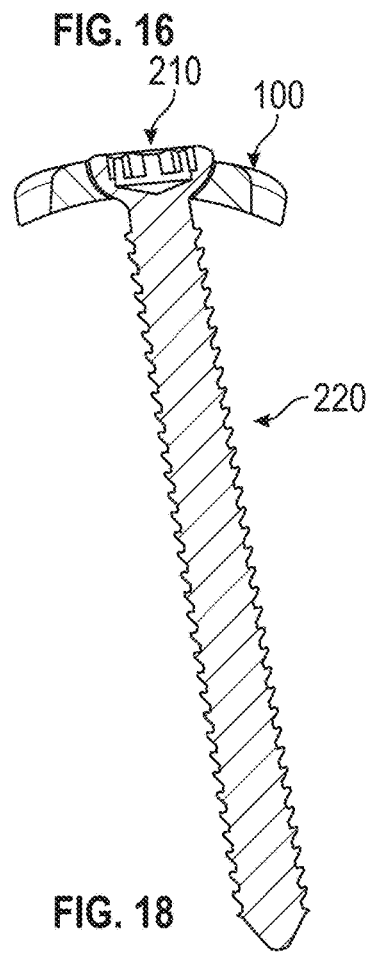
FIG. 18 is an enlarged sectional view of the bone screw 200 locked into the screw hole 130 of the bone fixing plate 100.
Figure 19:
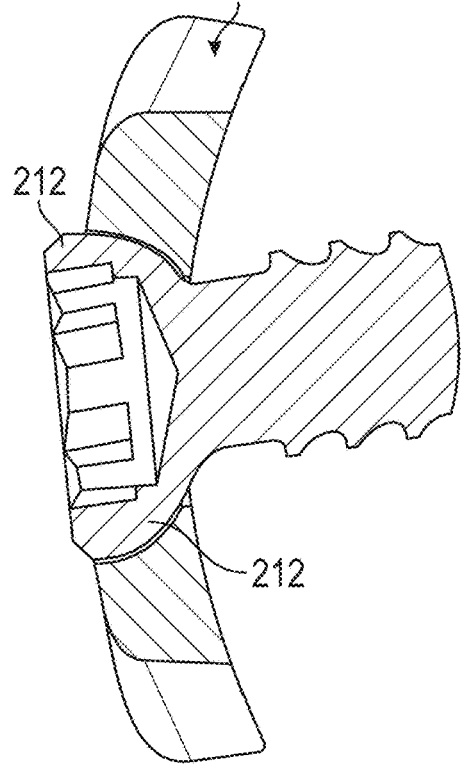
FIG. 19 is an enlarged view of the screw head 210 in a locked position within the screw hole 130.
Figure 20:
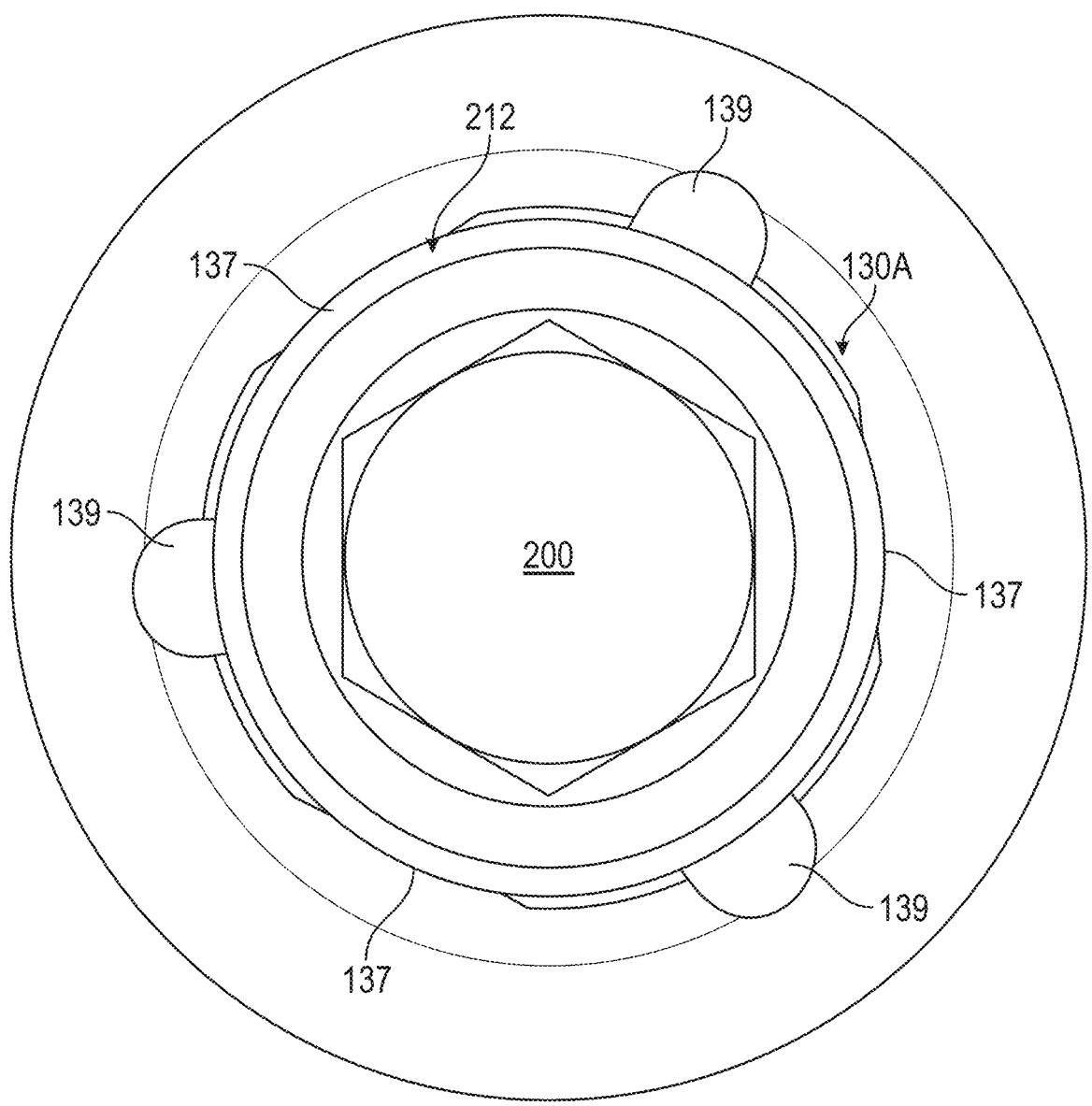
FIG. 20 is a top enlarged view of the bone screw head 210 in locked engagement with the screw hole 130.
Figure 21:
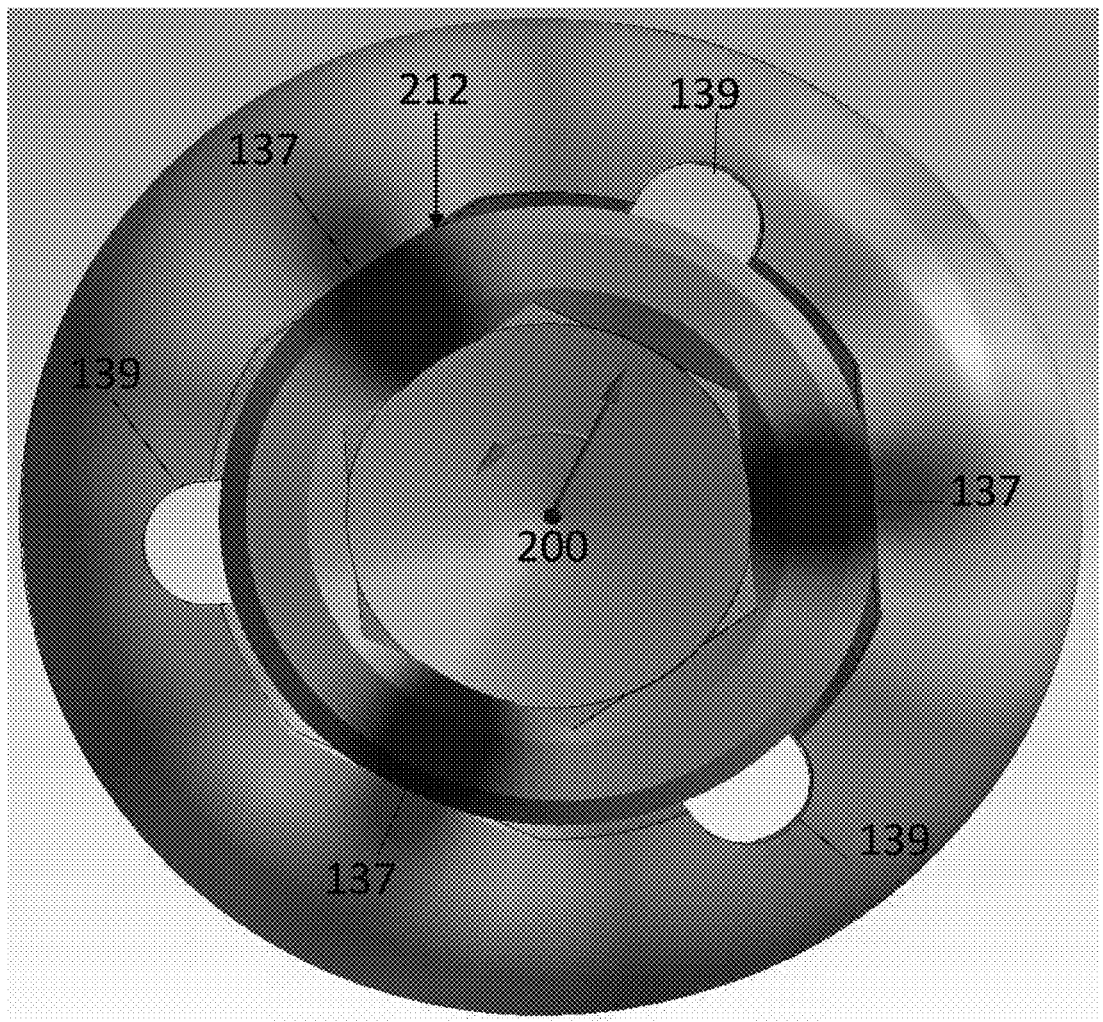
FIG. 21 denotes regions of deformation along interference portions 137 and parts of the upper rim 212 engaging with the interference portions 137.

FIGS. 1 to 21 illustrate a bone fixation system 1000 for reconstruction and/or trauma treatment of bones. FIGS. 1 to 6 in particular illustrate isolated views of the bone fixing plate 100. The bone plate 100 comprises substantially an upper surface 110 and a lower surface 120 intended to be closer to the bone than the upper surface 110, and a number of plate holes 130 that extend from upper surface 110 to the lower surface 120. Openings 130A and 130B are formed on the upper surface 110 and the lower surface 120 respectively to form a passage extending from the upper surface 110 to the lower surface 120 to allow a shank portion 220 of a bone screw 200 (shown in FIGS. 7 to 21) to pass through the passage and be engaged with the bone tissue (being repaired) and to allow the head 210 of the bone screw 200 to be engaged and locked with the non-threaded inner walls 135 defining the passage forming the plate hole 130. The engagement and locking mechanism of the bone screw 200 with the inner walls 135 will be explained in further detail in the foregoing sections.

The three inner walls 135, each comprise interference portions 137. In the preferred embodiment, the interference portions 137 are circumferentially arranged relative to the opening 130A on the upper surface of the bone fixing plate 100. As shown clearly in the top view of the plate hole 130 in FIG. 3, the interference portions 137 are arranged and dimensioned to define the width of the opening of the upper surface 110 into the passage 130 to be slightly smaller than an upper region 212 of the head 210 of the bone screw 200. Each plate hole 130 is defined by three inner walls 135 and adjacent inner walls 135 are separated from each other by recessed channels 139 that extend in a downwardly direction from the upper surface 110 to the lower surface 120. The inner walls 135 comprise a curved surface (that is substantially a concave spherical surface) and all three inner walls 135 converge in an in-use downwardly direction (extending from the upper surface 110 to the lower surface 120) to form a seat that can receive at least a lower curved portion 214 of the bone screw head 210. The seat formed by the convergent curved surfaces of the inner walls 135 is provided to receive and engage a lower portion of the screw head 210 and also prevent the screw head 210 from being inadvertently pushed out of the opening 130B in the lower surface 120 of the bone plate 100. The width of the opening 130B for the lower surface 120 is smaller than the width for the opening 130A and slightly larger than the width diameter (d2) (shown in FIG. 8A) of the shank portion 220 of the bone screw 200 to allow the shank 220 to be passed through.

The width for the opening of the upper surface 110 is large enough to allow the convergent lower spherical portion 214 of the bone screw 200 to pass through. Referring specifically to FIG. 8A, the upper region 212 of the screw head 210 is substantially cylindrical with a height (h1) and the overall diameter (d1) of the upper region 212 of the bone screw head 210 is dimensioned to be slightly greater than the width of the opening 130A of the upper surface 110. The slight difference between d1 and the width of the opening 130A results in interference between the upper region 212 of the screw head 210 of the bone screw 200 and the interference portions 137 of the inner walls 135 to lock the head 210 of the bone screw 200 within the passage 130 upon insertion of the bone screw 200 into the passage 130 at a variable angle of rotation relative to a longitudinal axis of the passage that is substantially perpendicular to the upper surface of the bone plate the head of the bone screw 200. In the preferred embodiment of the bone fixation plate 100, before undergoing deformation (as indicated by Lines Q in FIG. 22), the shortest distance between the planar surface for each interference portion 137 and the centre of the opening 130A is denoted by r. For the interference portions 137 to be engaged and deformed by the upper rim region 212 of the screw head 210, the diameter of the upper rim region 212 should preferably be slightly greater than 2r (twice the shortest distance between the planar surface for each interference portion 137).

Unlike the curved surface of the inner walls 135, the interference portions 137 comprise a planar configuration which reduces the width across the opening 130A of the upper surface 110 and results in deformation of the interference portion 137 and the inner walls 135 as the bone screw 200 passes through the passage 130 (at the variable angle of rotation) and the upper region 212 if the screw head 210 comes into contact with the planar surface of interference portions 137. The circumferentially arranged recessed channels 139 are configured and dimensioned to accommodate any deformation of the inner walls 135 and the interference portions 137 which is caused as a result of the interference portions 137 being engaged by the upper region of the screw head 210.

The upper cylindrical region 212 which is in the form of a rim has a height h1 and engages the interference portion 137 that has an overall length m1. In the preferred embodiment, the length m1 (shown in FIG. 6) of the interference portion 137 is independent of the height h1 of the rim region of the bone screw 200. However m1 must be chosen to allow inter-engagement between the upper rim region 212 of the bone screw head 210 and the interference portions 137 of the inner walls 135 when the bone screw 200 is inserted at a plurality of different angular orientations.

The bone plate 100 and the bone screw 200 can be made from metal, a resorbable or non-resorbable plastic, ceramic, or composite materials. Suitable materials may include, for example, titanium, stainless steel, cobalt chrome, polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body.

Turning now to the methods of implantation, the surgeon accesses the surgical site of interest, which can be an internal site at which a bone fracture is located that requires stabilization to ensure proper healing. The fracture may be reduced with conventional forceps and guides (which are known to those in the art), and a bone plate such as but not limited to the specific configuration of the bone plate 100 may be placed over the fracture site. The bone plate such as the bone plate 100 may comprise of a plurality of plate holes 130 arranged like a string of pearls to suit the specific site of interest. The number of plate holes 130 provided in the bone plate 100 is not limiting. Similarly, the configuration of the bone plate 100 specifically the solid regions of the plate 100 between the plate holes 130 may be curved or bent and therefore the bone plate 100 may be formed in a variety of different configurations.

In some instances, the bone plate 100 may be temporarily secured to the bone (not shown) using provisional fixation pins. The provisional fixation pins may be used through either the provisional pin openings, or any other openings on the plate 100. For ease of explanation, the provisional pin openings have not been shown in the figures. Provisional fixation provides for temporarily securing the bone plate 100 to the bone before placing bone fixation screws 200 through the bone plate 100, so that one can be certain the bone plate 100 is properly positioned before placing bone screws for permanent fixation of the bone plate 100 to the bone.

Once the bone plate 100 is secured at a desired location in relation to the fracture (typically using one or more provisional fixation pins, although any other appropriate method may be used), the surgeon then identifies an insertion angle at which the bone screw 200 is to be inserted through the plate hole 130 and driven into bone tissue. After selecting the desired insertion angle and the plate hole 130, the surgeon inserts the shaft 220 of the fastener bone screw 200 through the opening 130 until the tip 225 of the shank 220 contacts bone tissue. In some cases, a hole may need to be pre-drilled or tapped into the bone tissue along the chosen insertion angle to facilitate the initial tapping or insertion of the bone screw 200. The surgeon then uses an appropriate driving tool to apply rotational torque to the screw head 220. The screw head 210 may be provided with an appropriate driver engaging interface. In the preferred embodiment, the bone screw 200 is provided with a hexagonal head for interfacing with the driving tool. It would be understood that the hexagonal head configuration is not limiting and any other suitable configuration such as but not limited to a torx head interface may also be provided in alternative embodiments.

It is important to note that the configuration of the bone plate 100, particularly the provision of the interference portions 137 along the upper portions of the inner walls 135 allows the screw head 210 to be locked within the plate hole 130 at a plurality of orientations. In this instance, the bone screw 200 may be inserted at angles such as in the range of 1 to 30 degrees in any direction (as shown in FIGS. 16 to 19) from the perpendicular to the upper surface 110 or the lower surface 120 of the plate 100. The shank portion 220 when inserted at an angle is used to grab and/or secure bone fragments that are out of line with the traditional angle at which a locking screw would normally be inserted. The surgeon may need to toggle or manoeuvre the bone screw 200 in order to secure and draw in displaced bone fragments. In some instances, the surgeon may need to pull out the bone screw 200 and re-insert the bone screw 200 at a slightly different insertion angle to ensure that the bone fragments are held together under compression from the bone screw 200.

Figure 22:
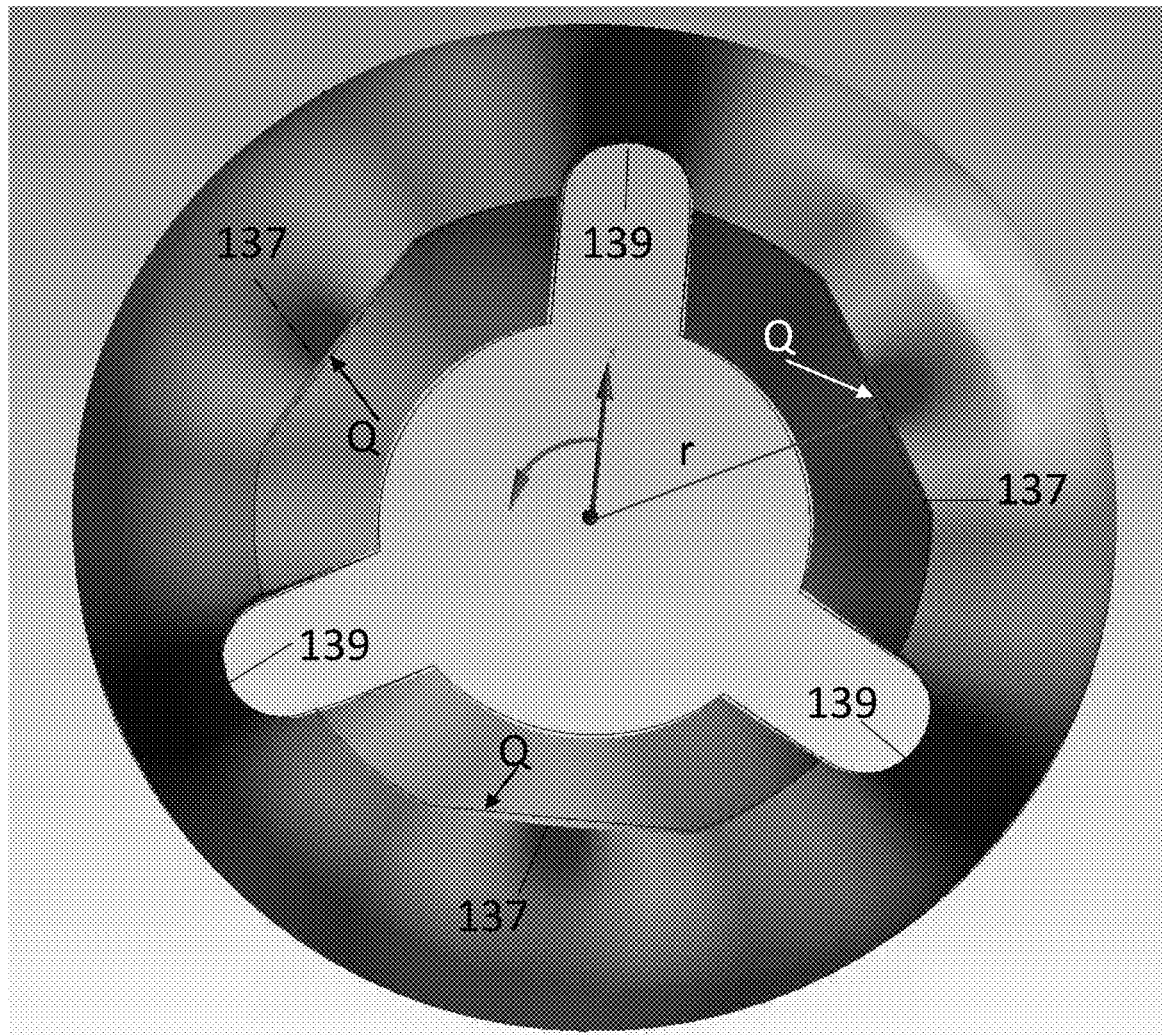
FIG. 22 shows an isolated top view of the screw hole 130. Each interference portion 137 has been shown in a slightly deformed position relative to its initial position denoted by line Q.

Through extensive trials and experiments, the inventor has found that the provision of the deformable interference portions 137 in the configuration as previously described, allows the locking arrangement provided by the interference portions 137 to be re-used for locking the screw head 210 at a slightly different angle of orientation without significantly damaging the locking arrangement provided by the interference portions. Without being bound by theory, it is hypothesized that on first instance, when the upper rim region 212 engages one or more of the interference portions 137, both the upper rim region 212 and the contacting interference portions 137 undergo some level of deformation which may be elastic deformation. When the bone screw 200 is pulled out by applying rotational torque in the reverse direction, the interference portion 137 and the upper rim region 212 are no longer under engagement which may result in the interference portion 137 and the upper rim region 212 of the bone screw 200 fully returning to its original dimensions (under elastic deformation). In other instances, the interference portions 137 and the upper rim region 212 of the screw head 210, upon interference may undergo plastic deformation and after removal of the bone screw 200, the interference portion 137 and the upper rim region 212 of the screw 210 may only partially return to their original dimensions. It is theorised that providing a locking mechanism for the screw head 210 that relies on interference and elastic deformation of the interference portions 137 and the upper rim region 212 of the screw head 210 allows the screw hole 130 in the bone plate 100 to be used repeatedly for engaging the screw head 210 of a bone screw 200 at a variety of angles. The deformation mode of locking the screw head 210 provided by the bone fixing plate 100 allows the screw holes 130 to be utilised repeatedly. Of course, it would also be appreciated by a skilled person that many materials particularly metals cannot undergo elastic deformation infinite number of times. At least in some instances particularly when the bone fixing plate 100 and the bone screw 200 are formed from metallic materials, after been subjected to repeated stresses, the interference portions 137 and/or the upper rim region 212 of the screw head 212 may undergo metal fatigue and as a result may not completely recover to their original dimensions. FIG. 22 shows a top view of a plate hole 130 that has undergone deformation after repeated use. The outline denoted by lines Q across each interference portion illustrates the structural configuration of the interference portions 137 before undergoing deformation and the shaded regions for the interference portions 137 denote deformed parts of the interference portions 137. In comparison, many of the locking mechanisms known for variable angle locking plates are often limited to one-time use because the threads provided on the screw head and inner walls for plate holes of such prior art systems get damaged after being used in the first instance. The bone fixation system 100 addresses this shortcoming.

Once the bone fragment is secured by the threads provided on the shank portion 220 of the bone screw, the screw head 210 is locked to the inner walls 135 of the screw hole 130 in the bone plate 100. The interference portions 137 are located along an upper portion of each inner wall 135 in close proximity to the opening 130A of the upper surface 110. As explained earlier, the interference portions 137 engage with the upper rim region 212 of the screw head 210. As a result, the locking mechanism is engaged only after the shank 220 (with the threads for effecting compression of the bone fragments) of the bone screw 200 has passed through the plate hole 130 and the lower head portion 214 is at least partially seated along the curved surface of the inner walls.

The location of the interference portions 137 and the rim 212 of the screw head 212 allows the bone fragments to be held under compression and push the bone fixing plate 100 onto the surface of the bone tissue before locking the screw head 210 with the plate hole 130. In some prior art systems that allow variable angle locking, the screw head for bone screws of such systems locks with the plate before the plate has been fully pushed onto the surface of the bone tissue under compression. The bone fixation system 1000 addresses this issue.

The configuration of the locking system provided by the interference portions 137 and the screw head 210 also allows the thickness of the bone fixing plate 100 to be lesser than bone fixing plates used for some of the known bone fixation systems that provide variable angle locking. The lowering in thickness for the bone fixing plate 100 has been achieved by providing the locking mechanism only in the upper region of the plate hole 130. Many other prior art bone fixation systems use plates with plate holes where by the entire height of the plate hole (and thickness of the bone fixing plate) is utilised for variable angle locking.

It would be understood by a skilled person that in some instances only some of the plate holes 130 may be used in conjunction with locking bone screw screws 200. The surgeon may place covers over the unused openings, particularly if there are any unused openings that cross the fracture, to strengthen the plate 100. Additionally or alternatively, the surgeon may also use bone graft material, bone cement, bone void filler, and any other material to help heal the bone.

A number of implementations of the invention have been described. Nevertheless, it will be understood that various modifications may be made without departing from the spirit and scope of the invention. Accordingly, other implementations are within the scope of the following claims. For example, locking screws, non-locking screws, or other fasteners may be used. It also to be understood that in at least some embodiments, the bone screw 200 may be inserted in a substantially perpendicular orientation as shown in FIGS. 12 to 15 which may result in the engagement of all three interference portions 137 with the upper rim region 212 of the bone screw 200 to provide a locking mechanism in a manner as has been explained in the previous sections.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

The invention claimed is:

1. A bone fixation system for treatment of bones, the bone fixation system comprising:
   a bone screw having a head with a diameter;
   a bone fixation plate configured and dimensioned for application to a patient's bone, the bone fixation plate comprising:
      an upper surface and a lower surface;
      at least one opening formed on each of the upper surface and the lower surface;
      a passage formed by the openings on the upper surface and the lower surface, the passage having a longitudinal axis and a width, the passage extending from the upper surface to the lower surface each passage being defined by one or more non-threaded inner walls having a continuous surface extending from the upper surface to the lower surface of the bone fixation plate to receive the bone screw, wherein portions of the one or more non-threaded walls comprise a curved surface, and wherein adjacently located non-threaded inner walls are separated by a recessed channel; and
   resiliently deformable interference portions located along an upper portion of the one or more non-threaded inner walls of the passage, the resiliently deformable interference portions defining the opening on the upper surface such that the opening is smaller than the diameter of the head of the bone screw, the resiliently deformable interference portions comprising a substantially planar surface positioned for abutment with an upper rim of the head of the bone screw, the resiliently deformable interference portions being dimensioned to define the width of the passage to be smaller than the diameter of the head of the bone screw to achieve deformation of the interference portions and interference between the head of the bone screw and the non-threaded inner walls to lock the head of the bone screw within the passage upon insertion of the bone screw into the passage at a variable angle of rotation relative to a longitudinal axis of the passage that is substantially perpendicular to the upper surface of the bone fixation plate.

2. The bone fixation system of claim 1, wherein the recessed channel extends between the upper surface and the lower surface of the bone fixation plate.

3. The bone fixation system of claim 1, wherein the recessed channel is substantially parallel to the longitudinal axis of the passage.

4. The bone fixation system of claim 1, further comprising a plurality of said recessed channels, the recessed channels being circumferentially arranged relative to the at least one opening of the bone fixation plate.

5. The bone fixation system of claim 1, wherein the one or more non-threaded inner walls comprises a concave surface.

6. The bone fixation system of claim 5, wherein the upper portions of one or more of the non-threaded inner walls comprise a concave spherical surface.

7. The bone fixation system of claim 6, wherein said upper portions of one or more non-threaded inner walls converge towards each other in a downwardly direction from the upper surface to the lower surface thereby decreasing the width of the passage in the downwardly direction.

8. The bone fixation system of claim 1, wherein the width of the passage gradually deceases in a downwardly direction from the upper surface to the lower surface.

9. The bone fixation system of claim 1, wherein the non-threaded inner walls define a convergent passage converging towards the lower surface of the bone fixation plate to seat the head of the bone screw, and allowing the upper portion of the inner walls to engage with the head of the bone screw.

10. The bone fixation system of claim 1, wherein each said interference portion is located in an upper portion of the corresponding non-threaded inner wall.

11. The bone fixation system of claim 1, wherein a plurality of said interference portions circumferentially arranged along the non-threaded inner walls defines the passage such that upon insertion of the bone screw at a variable angle of rotation relative to a longitudinal axis of the passage that is substantially perpendicular to the upper surface of the bone plate and the head of the bone screw engages one or more of said portions thereby locking the head of the bone screw with the inner walls.

12. The bone fixation system of claim 1, wherein the interference portions of the inner wall are formed from deformable material such that when the bone screw is inserted into the passage, said interference portions deform to allow the head of the bone screw to be locked into the passage.

13. The bone fixation system in accordance of claim 1, wherein at least one of the openings comprises a bevelled edge or a filleted edge.

14. A method of affixing a bone screw to a bone fixation plate at a desired orientation, comprising the steps of:
providing a bone screw, the bone screw comprising:
a non-threaded head portion with a driver engaging interface, the non-threaded head portion having a diameter; and
an elongate threaded shank section comprising helical threads, the elongate threaded shank section adjoining the non-threaded head portion;
providing a bone fixation plate, the bone fixation plate comprising:
an upper surface and a lower surface;
at least one opening formed on each of the upper and lower surfaces
a passage formed by the openings on the upper surface and the lower surface, the passage having a longitudinal axis, the passage extending from the upper surface to the lower surface; each passage is defined by one or more non-threaded inner walls that have a continuous surface from the upper surface to the lower surface, wherein portions of the one or more non-threaded walls comprise a curved surface, and wherein adjacently located non-threaded inner walls are separated by a recessed channel; and
resiliently deformable interference portions located at an upper portion of the one or more non-threaded inner walls of the passage; the resiliently deformable interference portions defining the opening on the upper surface such that the opening is smaller than the diameter of the non-threaded head portion of the bone screw, the resiliently deformable portions comprising a substantially planar surface positioned for abutment with an upper rim of the non-threaded head portion of the bone screw;
positioning said bone fixation plate on bone tissue such that the lower surface of the bone fixation plate is positioned to contact and engage the bone tissue and positioning the upper surface is positioned to receive the elongate threaded shank section of the bone screw;
selecting one of a plurality of different insertion angles at which the bone screw is to be inserted into the passage of the bone fixation plate;
inserting the elongate threaded shank section of the bone screw into the passage at the selected insertion angle; and
applying drive to the non-threaded head portion of the bone screw until interference is achieved between an outer surface of the non-threaded head portion of the bone screw and the interference portions of the bone fixation plate to deform the interference portions and lock the non-threaded head portion of the bone screw within the passage.

* * * * *